United States Patent [19]
Ritchie et al.

[11] Patent Number: 6,015,905
[45] Date of Patent: Jan. 18, 2000

[54] PROCESS FOR THE PREPARATION OF 2-(6-SUBSTITUTED PYRID-2-YLOXYMETHYL) PHENYLACETATE

[75] Inventors: David John Ritchie, Falkirk; Gordon Richard Munns, Earley; Julie Forrester, Larbet; Michael Charles Henry Standen, Clackmannan; Paul Anthony Worthington, Maidenhead; Raymond Vincent Heavon Jones, Linlithgow, all of United Kingdom

[73] Assignee: Zeneca Limited

[21] Appl. No.: 08/973,252

[22] PCT Filed: Jun. 3, 1996

[86] PCT No.: PCT/GB96/01311

§ 371 Date: Dec. 2, 1997

§ 102(e) Date: Dec. 2, 1997

[87] PCT Pub. No.: WO97/01538

PCT Pub. Date: Jan. 16, 1997

[30] Foreign Application Priority Data

Jun. 28, 1995 [GB] United Kingdom .................. 9513113
Jan. 31, 1996 [GB] United Kingdom .................. 9601875

[51] Int. Cl.[7] ...................... C07D 213/64; C07D 213/69; C07D 213/70; C07D 213/84
[52] U.S. Cl. .................. 546/288; 546/292; 546/296; 546/297; 546/298; 546/302
[58] Field of Search .................. 546/302, 288, 546/292, 296, 297, 298

[56] References Cited

U.S. PATENT DOCUMENTS

| | | | |
|---|---|---|---|
| 5,008,438 | 4/1991 | Schuetz et al. | 560/55 |
| 5,057,146 | 10/1991 | Anthony et al. | 504/255 |
| 5,077,303 | 12/1991 | Seele et al. | 514/336 |
| 5,157,037 | 10/1992 | Schuetz et al. | 514/336 |
| 5,166,216 | 11/1992 | Schuetz et al. | 514/406 |
| 5,194,622 | 3/1993 | Brayer et al. | 548/204 |
| 5,334,577 | 8/1994 | Wenderoth et al. | 504/130 |
| 5,606,095 | 2/1997 | Pfiffner et al. | 560/42 |

FOREIGN PATENT DOCUMENTS

| | | |
|---|---|---|
| 42121/93 | 1/1994 | Australia . |
| 0 299 694 | 1/1989 | European Pat. Off. . |
| 0 378 308 | 7/1990 | European Pat. Off. . |
| 0 611 760 | 8/1994 | European Pat. Off. . |
| 94/22833 | 10/1994 | WIPO . |

OTHER PUBLICATIONS

Comins, D. L., et al., Tetrahedron Letters, "N–vs. O–Alkylation in the Mitsunobu Reaction of 2–Pyridone," vol. 35, No. 18, 1994, pp. 2819–2822.

Hopkins, George C., et al., J. Org. Chem., "Alkylations of Heterocyclic Ambident Anions. II. Alkylation of 2–Pyridone Salts," vol. 32, 1967, pp. 4040–4044.

Shiao, Min–Jen et al., Heterocycles, "A Facile Synthesis of Bromo–2–Alkoxypyridines," vol. 31, No. 5, 1990, pp. 819–824.

Chemical Abstracts, No. 89133q, vol. 98, (1983).
Chemical Abstracts, No. 39238e, vol. 87, (1977).
Chemical Abstracts, No. 77781k, vol. 81, (1974).
Chemical Abstracts, No. 55938z, vol. 73, (1977).
Chemical Abstracts, No. 12505t, vol. 72, (1970).

*Primary Examiner*—Alan L. Rotman
*Attorney, Agent, or Firm*—David P. LeCroy

[57] ABSTRACT

A process for preparing 2-(6-substituted pyrid-2-yloxymethyl)phenyacetates especially useful as intermediates for producing agricultural fungicides. The invention provides a compound having the formula (I):

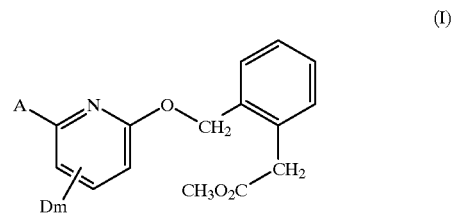

(I)

wherein A and D are independently selected from the group comprising halo, hydroxy, halo($C_{1-4}$)alkyl, $C_{1-4}$alkoxy, thio ($C_{1-4}$)alkoxy, halo($C_{1-4}$)alkoxy, phenyl, phenoxy, nitro, amino, aclyamino, cyano, carboxy, $C_{1-4}$ alkoxycarbonyl and $C_{1-4}$ alkylcarbonyloxy, or D is $C_{1-4}$ alkyl, and m is 0 or an integer of from 1 to 3. The process comprises treating a compound of formula (II):

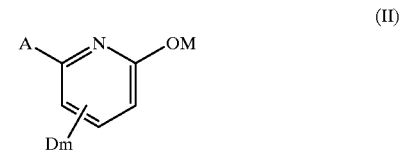

(II)

wherein A, D and m are defined as above and M is a metal atom, with a compound of formula (III):

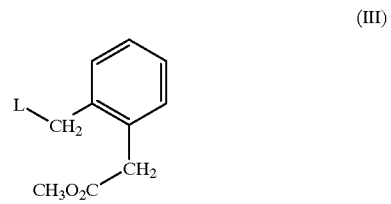

(III)

wherein L is a leaving group.

8 Claims, No Drawings

PROCESS FOR THE PREPARATION OF 2-(6-SUBSTITUTED PYRID-2-YLOXYMETHYL) PHENYLACETATE

CROSS-REFERENCE

This application is a 371 of PCT/GB96/01311 filed Jun. 3, 1998.

The present invention relates to a chemical process and, more particularly, to a process for preparing 2-(6-substituted pyrid-2-yloxymethyl)phenylacetates. These compounds are useful as intermediates for producing agricultural fungicides.

Some new agricultural fungicides, which are methyl 2-[2-(aryl- and heteroaryloxymethyl)phenyl]-3-methoxyacrylates, are described in EP-A-0278595 along with a variety of methods for their preparation.

One method of preparation involves the conversion of a methyl 2-halomethylphenylacetate to a methyl 2-aryl- or 2-heteroaryloxymethylphenylacetate by treatment with an alkali metal salt of a phenol or appropriate hydroxy heteroaromatic compound, followed by the transformation of the methyl acetate group into a methyl methoxyacrylate.

A disadvantage of this method is that in using it to prepare the compound methyl 2-(pyrid-2-yloxymethyl) phenylacetate by treating 2-bromomethylphenyl-acetate with 2-pyridone in the presence of an alkali metal hydroxide, substantial amounts of the unwanted N-alkylated product are obtained.

The N- and O-alkylation of pyridones and factors which influence their formation are discussed in "Pyridine and Its Derivatives, Part Three", Ed. E Klingsberg, 1962, John Wiley & Sons, pages 630–633 and in "Pyridine and Its Derivatives, Supplement Part Three", Ed. R A Abramovitch, John Wiley & Sons, pages 745–749. In particular, it is noted that the introduction of a 6-methyl substituent into 2-hydroxypyridine reduces the amount of N-benzylation from 50% to 16%.

Unfortunately, the presence of an acetate group in the 2-position of the benzylating agent can lead to the formation of unwanted dimeric material as a result of the interaction of two molecules of the benzylating agent. Although N-benzylation is reduced by the presence of a 6-methyl substituent, dimerisation predominates and very little of the desired O-benzylated product is obtained.

It has now been found that both N-alkylation and dimerisation can be substantially reduced, and N-alkylation even eliminated for all practical purposes, by including a substituent other than alkyl in the 6-position of the pyridine ring.

Accordingly, the present invention provides a process for the preparation of a compound of formula (I)[1] wherein A and D are independently selected from the group comprising halo (especially fluoro, chloro or bromo), hydroxy, $C_{1-4}$ alkyl (especially methyl or ethyl), halo($C_{1-4}$)alkyl (especially halomethyl, particularly trifluoromethyl, difluoromethyl, fluoromethyl or trichloromethyl), $C_{1-4}$ alkoxy (especially methoxy), thio($C_{1-4}$)alkoxy (especially thiomethoxy), halo($C_{1-4}$)alkoxy (especially trifluoromethoxy), phenyl, phenoxy, nitro, amino, acylamino (especially formamido or acetylamino), cyano, carboxy, $C_{1-4}$ alkoxycarbonyl (especially methoxycarbonyl) and $C_{1-4}$ alkylcarbonyloxy (especially acetoxy) and m is 0 or an integer of from 1 to 3, which comprises treating a compound of formula (II), wherein A, D and m are as defined above and M is a metal atom, with a compound of formula (III) wherein L is a leaving group. Where m is 2 or 3 so that D represents 2 or 3 substituents, these substituents may be the same or different.

[1] Seee Chemical Structures at the end of this specification.

Halo is typically fluoro, chloro or bromo.

Alkyl and the alkyl moiety of alkoxy, alkoxycarbonyl and alkylcarbonyloxy contain from 1 to 4 carbon atoms in the form of straight or branched chains. Examples are methyl, ethyl, n- and iso-propyl, n-, sec-, iso- and tert-butyl. Examples of halo-substituted alkyl groups are halomethyl and haloethyl, which include trifluoromethyl, difluoromethyl, fluoromethyl, trichloromethyl, dichloromethyl, chloromethyl and pentafluoroethyl. Examples of haloalkoxy are trifluoro- and trichloromethoxy. Examples of alkoxycarbonyl and alkylcarbonyloxy are methoxycarbonyl and acetoxy.

Acylamino includes, in particular, $C_{1-4}$alkanoylamino, for example, formamido and acetylamino.

Phenyl and phenoxy groups may themselves be substituted by one or more substituents. Suitable substituents include, for example, halo, $C_{1-6}$ alkyl, halo($C_{1-4}$)alkyl, $C_{1-4}$ alkoxy, thio($C_{1-4}$)alkoxy, halo($C_{1-4}$)alkoxy, phenyl, phenoxy, cyano, nitro, amino, mono- or di-($C_{1-4}$)alkylamino, $C_{1-4}$ alkanoylamino, carboxy, $C_{1-4}$ alkoxycarbonyl or $C_{1-4}$ alkylcarbonyloxy.

The leaving group L is any suitable leaving group for ether formation with a pyridone. Examples include halide (chloride, bromide or iodide), a $CH_3SO_4$ anion, and a sulphonyloxy anion. Bromide is particularly suitable. Typically it will be bromide or chloride.

The metal atom M is usually an alkali metal or alkaline earth metal atom or a metal atom such as silver. Typically it will be sodium, potassium or silver.

In another aspect the invention provides a process for preparing a compound of formula (I), wherein A and D are as defined above and m is 0 or 1, which comprises treating a compound of formula (II), wherein A, D and m are as defined above, with a compound of formula (III), wherein L is as defined above.

Where m is 1, D is attached to, for example, the 4-position of the pyridine ring.

In yet another aspect, the invention provides a process for preparing a compound of formula (I) wherein A and D are independently selected from the group comprising halo (especially chloro or bromo), $C_{1-4}$ alkyl (especially methyl), halo($C_{1-4}$)alkyl (especially trifluoromethyl) and $C_{1-4}$ alkoxy (especially methoxy), m is 0 or 1, and where m is 1, D is attached to the 4-position of the pyridine ring, which comprises treating a compound of formula (II), wherein A and D are as defined above and M is a metal atom, with a compound of formula (III) wherein L is a leaving group. Preferably, A is other than $C_{1-4}$ alkyl.

The invention process is conveniently carried out by treating an appropriate 6-substituted 2-pyridone with the compound of formula (III) in the presence of a base such as sodium hydroxide or potassium carbonate, and in a suitable solvent. Alternatively, a preformed metal salt of the 6-substituted 2-pyridone may be treated with the compound of formula (III) in a suitable solvent with or without a base being present. Suitable solvents include aromatic hydrocarbon solvents such as toluene, xylene or benzene and polar aprotic solvents such as N,N-dimethyl formamide and butanone. If the 6-substituted 2-pyridone is used in the form of a water wet paste, water may be removed by azeotropic distillation with a suitable mixture partner such as toluene.

The metal salt of the 6-substituted 2-pyridone is conveniently prepared by treating the pyridone with an alkali metal base such as an alkali metal hydroxide or carbonate in a suitable solvent such as toluene or butanone, at an elevated temperature, for example, at the reflux temperature of the solvent. The metal salt formation may be assisted by, for example, the use of a crown ether. If desired, the salt can be isolated by removal of the solvent under reduced pressure.

The metal salt or the pyridone and base are conveniently dissolved or slurried in a suitable solvent such as N,N-dimethylformamide or butanone and the compound of formula (III) which may also be dissolved in the same or a compatible solvent, added stepwise. The reactants are stirred together at a temperature usually in the range of from 10 to 100° C., for example, at ambient temperature, around 20° C., or at temperatures in the range of from 60 to 90° C., typically from 70 to 80° C., and optionally in the presence of a reaction assistant such as sodium iodide or sodium bromide or a phase transfer catalyst such as tetrabutylammonium iodide. When the reaction is complete, as adjudged, for example, by TLC or GC analysis of samples taken periodically from the reaction mixture, the product may be isolated by pouring the mixture into water or adding water to the mixture and extracting it with a suitable solvent such as diethyl ether or toluene. The solvent extract can then be washed and dried and the product isolated by removal of the solvent under reduced pressure. It may be found advantageous to remove the reaction solvent by distillation before isolation of the product.

The use of potassium carbonate as the base for forming the metal salt of the 6-substituted 2-pyridone has been found to offer advantages in terms of product yield.

The 6-substituted 2-pyridones used in the process of the invention are either already commercially available or can be prepared from commercially available materials by methods well documented in the chemical literature. In one useful method of preparation, the corresponding 2-chloropyridine is hydrolysed to the 2-pyridone using sodium hydroxide in a convenient solvent such as dimethyl sulphoxide and water.

The compound of formula (III) wherein L is halogen, such as bromine or chlorine, may be prepared by halogenation of the corresponding methylphenylacetate using, for example, N-bromosuccinimide or sulphuryl chloride and methods described in the literature (see, for example, *Modern Synthetic Reactions*, Herbert House, 2nd Edition, Benjamin/Cummings, p.478 and references therein, and H. Matsumoto et al., *Chemistry Letters*, 1978, pp.223–226). Phenylacetates of formula (III) wherein L is a sulphonyloxygroup, may be prepared from the corresponding hydroxymethylphenylacetate using a sulphonyl halide and methods described in the literature. Treatment of benzyl alcohols with sulphonyl halides in the presence of a base sometimes leads, via a sulphonyloxy derivative, to a benzyl halide, and this constitutes an alternative approach to compounds of formula (II) wherein L is a halogen.

Alternatively, 3-isochromanones may be converted into the phenylacetates of formula (III) wherein L is a halogen atom (such as bromine), using HL in methanol. This transformation may also be accomplished in 2 steps if the isochromanone is treated with HL in a non-alcoholic solvent, and the resulting phenylacetic acid is then esterified using standard procedures (see, for example, I Matsumoto and J Yoshizawa, Jpn. Kokai (Tokkyo Koho) 79 137 536, 27.10.1979, *Chem. Abs.*, 1980, 92, 180829h; and G M F Lim, Y G Perron and R D Droghini, *Res. Discl.*, 1979, 188, 672, *Chem. Abs.*, 1980, 92, 128526t).

The product of the invention process is a useful intermediate for the preparation of agricultural fungicides, such as those described in EP-A-0278595. Processes for preparing these fungicides from the intermediates by formylation and methylation are fully described Examples of the compounds of formula (I) prepared by the process of this invention are illustrated in Table 1.

TABLE 1

| Compound No. | A | D | m |
| --- | --- | --- | --- |
| 1 | Cl | — | 0 |
| 2 | Br | — | 0 |
| 3 | $CF_3$ | — | 0 |
| 4 | $CH_3O$ | — | 0 |

These phenylacetates (I) were converted by formylation and methylation to the agricultural fungicides (IV) as illustrated in Table 2.

TABLE 2

| Phenylacetate (I) (Compound No. in Table 1) | A | D | m | Final Product (Compound No. in Table 1 of EP-A-0278595) | Olefinic* | mp (° C.) |
| --- | --- | --- | --- | --- | --- | --- |
| 1 | Cl | — | 0 | 244 | 7.56 | 91–92 |
| 2 | Br | — | 0 | 176 | 7.56 | 64–65 |
| 3 | $CF_3$ | — | 0 | 177 | 7.55 | 73–74 |
| 4 | $CH_3O$ | — | 0 | 78 | | |

*Chemical shift of singlet from olefinic proton on β-methoxypropenoate group (ppm from tetramethylsilane).

The following Examples illustrate the invention. Unless otherwise stated, magnesium sulphate was used to dry solutions, solutions were concentrated under reduced pressure, reactions involving water-sensitive reagents were performed under an atmosphere of nitrogen and solvents were dried before use, where appropriate. Chromatography was performed on a column of silica gel as the stationary phase and NMR spectrum were recorded using. $CDCl_3$-solutions. The following abbreviations are used throughout:

| | |
| --- | --- |
| DMF = N,N-dimethylformamide | s = singlet |
| mp = melting point | d = doublet |
| NMR = nuclear magnetic resonance | m = multiplet |
| ppm = parts per million | |

EXAMPLE 1

This Example illustrates the preparation of methyl 2-(6-chloropyrid-2-yloxymethyl)phenylacetate (Compound No.1 in Table 1) and its conversion to the corresponding 3-methoxyacrylate (Compound No.244 in Table I of EP-A-0278595).

A mixture of 2-hydroxy6-chloropyridine (0.84 g, 6.5 mmol), sodium hydroxide (0.275 g, 6.9 mmol) and 15-crown-5 (1 drop) in dry toluene (15 ml) were stirred at reflux for 1.5 hours. The toluene was removed under reduced pressure and the white salt residue was dissolved in dry DMF (10 ml). Methyl 2-bromomethylphenylacetate (1.5 g, 6.2 mmol) in dry DMF (10 ml) was added dropwise along with sodium iodide (10 mg). The mixture was stirred at room temperature for 2 hours, poured into water and extracted with diethyl ether. The ether extracts were washed with water, dried and the ether removed in vacuo leaving a yellow oil which was purified by column chromatography (silica eluted with 10 % ethyl acetate in hexane) to give methyl 2-(6-chloropyrid-2-yloxymethyl)phenylacetate (1.11 g, 61%) (Compound No. 1 in Table 1) as a pale yellow oil; $^1$H NMR(270 MHz)δ:3.67(3H,s), 3.82(2H,s), 5.39(2H,s) 6.65 (1H,d), 6.90(1H,d), 7.25–7.55(5H,m) ppm.

Sodium methoxide (0.39 g, 6.9 mmol) and methyl formate (1 ml, 16 mmol) were added portionwise to a stirred solution of methyl 2-(6-chloropyrid-2-yloxymethyl) phenylacetate (1.0 g, 3.3 mmol) in dry toluene (15 ml) under a nitrogen atmosphere at room temperature. After 3 hours at room temperature the mixture was poured into water and extracted with ethyl acetate. The ethyl acetate extracts were washed with water, dried and the ethyl acetate removed to give (E)-methyl 2-[2-(6-chloropyrid-2-yloxymethyl) phenyl]-3-hydroxyacrylate (1.04 g, 95%) as a brown gum which was used in the final stage without further purification; $^1$H NMR(270 MHz)δ: 3.75(3H,s), 5.29(2H,s), 6.65 (1H,d), 6,90(1H,d), 7.15–7.60(6H,m), 11.98(1H,d) ppm.

Dimethyl sulphate (0.4 ml, 4.2 mmol) was added dropwise to a mixture of (E)-methyl 2-[2-(6-chloropyrid-2-yloxymethyl)phenyl]-3-hydroxyacrylate (1.04 g, 2.9 mmol) and anhydrous potassium carbonate (0.78 g, 5.6 mmol) in dry DMF (10 ml). After stirring at room temperature for 3 hours, the mixture was poured into water and extracted with ethyl acetate. The ethyl acetate extracts were washed with water, dried and concentrated to give an oil which was purified by column chromatography (silica eluted with 20% ethyl acetate in hexane) to give (E)-methyl 2-[2-(6-chloropyrid-2-yloxymethyl)phenyl]-3-methoxyacrylate (Compound No.244 in Table I of EP-A-0278595) (0.72 g, 74%) as a cream solid; mp 91–92° C.; $^1$H NMR (270 MHz)δ: 3.69(3H,s), 3.83(3H,s), 5.26(2H,s), 6.63(1H,d), 6.90(1H,s), 7.15–7.55(5H,m), 7.56(1H,s) ppm.

EXAMPLE 2

This Example illustrates the preparation of methyl 2-(6-trifluoromethylpyrid-2-yloxymethyl)phenylacetate (Compound No.3 in Table 1) and its conversion to the corresponding 3-methoxyacrylate (Compound No.177 in Table I of EP-A-0278595).

A mixture of 2-hydroxy-6-trifluoromethylpyridine (2.0 g, 12.3 mmol), sodium hydroxide (0.52 g, 12.9 mmol) and 15-crown-5 (1 drop) in dry toluene (25 ml) were stirred at reflux for 2 hours. The toluene was removed under reduced pressure and the white salt residue was dissolved in dry DMF (15 ml). Methyl 2-chloromethylphenylacetate (2.44 g, 12.3 mmol) in dry DMF (15 ml) was added dropwise along with sodium iodide (10 mg). The mixture was stirred at 75° C. for 2 hours, poured into water and extracted with diethyl ether. The ether extracts were washed with water, dried and the ether removed in vacuo leaving an oil which was purified by column chromatography (silica eluted with 10% ethyl acetate in hexane) to give methyl 2-(6-trifluoromethylpyrid-2-yloxymethyl)phenylacetate (3.3 g, 83%) (Compound No.5 in Table 1) as a yellow oil; $^1$H NMR (270 MHz)δ: 3.68(3H,s), 3.84(2H,s), 5.46(2H,s), 6.89(1H, d), 7,20–7.70(6H,m) ppm.

Sodium methoxide (0.725 g, 13 mmol) and methyl formate (0.8 ml, 13 mmol) were added portionwise to a stirred solution of methyl 2-(6-trifluoromethylpyrid-2-yloxymethyl)phenylacetate (2.0 g, 6.0 mmol) in dry toluene (15 ml) under a nitrogen atmosphere at room temperature. After 6 hours at room temperature, the mixture was poured into water and extracted with diethyl ether. The ether extracts were washed with water, dried and the ether removed to give (E)-methyl 2-[2-(6-trifluoromethylpyrid-2-yloxymethyl)phenyl]-3-hydroxyacrylate (2.01 g, 95%) as a yellow gum which was used in the next stage without further purification; $^1$H NMR (270 MHz)δ: 3.75(3H,s), 5.34(2H,s), 6.90(1H,d), 7.15–7.75(7H,m), 11.95(1H,d) ppm.

Dimethyl sulphate (0.65 ml, 6.9 mmol) was added dropwise to a mixture of (E)-methyl 2-[2-(6-trifluoromethylpyrid-2-yloxymethyl)phenyl]-3-hydroxyacrylate (2.12 g, 6 mmol) and anhydrous potassium carbonate (1.2 g, 8.7 mmol) in dry DMF (10 ml). After stirring at room temperature for 6 hours, the mixture was poured into water and extracted with diethyl ether. The ether extracts were washed with water, dried and concentrated to give a crude product which was purified by column chromatography (silica eluted with 20% ethyl acetate in hexane) to give (E)-methyl 2-[2-(6-trifluoromethylpyrid-2-yloxymethyl)phenyl]-3-methoxyacrylate (Compound No.177 in Table I of EP-A-0278595); (1.01 g, 46%) as a cream solid; mp 73–74° C.; $^1$H NMR (270 MHz)δ: 3.68 (3H,s), 3.82(3H,s), 5.34(2H,s), 6.87(1H,d), 7.15–7.70(6H, m), 7.55(1H,s) ppm.

EXAMPLE 3

This Example illustrates the preparation of methyl 2-(6-bromopyrid-2-yloxymethyl)phenylacetate (Compound No. 2 in Table 1) and its conversion to the corresponding 3-methoxyacrylate (Compound No. 176 in Table I of EP-A-0278595).

A mixture of 2-hydroxy-6-bromopyridine (1.3 g, 7.5 mmol), sodium hydroxide (0.36 g, 9.0 mmol) and 15-crown-5 (1 drop) in dry toluene (20 ml) were stirred at reflux for 1.5 hours. The toluene was removed under reduced pressure and the white salt residue was dissolved in dry DMF (10 ml). Methyl 2-chloromethylphenylacetate (1.0 g, 5 mmol) in dry DMF (10 ml) was added dropwise along with sodium iodide (10 mg). The mixture was stirred at 80° C. for 2 hours, poured into water and extracted with diethyl ether. The ether extracts were washed with water, dried and the ether removed in vacuo leaving an orange oil which was purified by column chromatography (silica eluted with 10% ethyl acetate in hexane) to give methyl 2-(6-bromopyrid-2-yloxymethyl)phenylacetate (0.86 g, 51%) (Compound No. 2 in Table 1) as an orange oil; $^1$H NMR (270 MHz)δ: 3.68 (3H,s), 3.73(2H,s), 5.38(2H,s), 6.68(1H,d), 7.06(1H,d), 7.25–7.50(5H,m) ppm.

Sodium methoxide (0.34 g, 6.0 mmol) and methyl formate (1 ml, 16 mmol) were added portionwise to a stirred solution of methyl 2-(6-bromopyrid-2-yloxymethyl) phenylacetate (0.8 g, 2.3 mmol) in dry toluene (10 ml) under a nitrogen atmosphere at room temperature. After 8 hours at room temperature the mixture was poured into water and extracted with ethyl acetate. The ethyl acetate extracts were washed with water, dried and the ethyl acetate removed to give (E)-methyl 2-[2-(6-bromopyrid-2-yloxymethyl) phenyl]-3-hydroxyacrylate (0.82 g, 80%) as a brown gum which was used in the final stage without further purification; $^1$H NMR (270 MHz)δ: 3.74(3H,s), 5.28(2H,s), 6.66 (1H,d), 7.06(1H,d), 7.15–7.55(6H,m), 11.95(1H,d) ppm.

Dimethyl sulphate (0.5 ml, 5.3 mmol) was added dropwise to a mixture of (E)-methyl 2-[2-(6-bromopyrid-2-yloxymethyl)phenyl-3-hydroxyacrylate (0.82 g, 1.8 mmol) and anhydrous potassium carbonate (0.75 g, 5.4 mmol) in dry DMF (20 ml). After stirring at room temperature for 3 hours, the mixture was poured into water and extracted with ethyl acetate. The ethyl acetate extracts were washed with water, dried and concentrated to give an oil which was purified by column chromatography (silica eluted with 20% ethyl acetate in hexane) to give (E)-methyl 2[2-(6-bromopyrid-2-yloxymethyl)phenyl]-3-methoxyacrylate (Compound No. 176 in Table I of EP-A-0278595) (0.67 g, 98%) as an orange solid; m.p. 64–65° C.; $^1$H NMR (270 Hz)δ: 3.69(3H,s), 3.84(3H,s), 5.26(2H,s), 6.66(1H,d), 7.05 (1H,d), 7.15–7.55(5H,m), 7.56(1H,s) ppm.

EXAMPLE 4

This Example illustrates the preparation of methyl 2-chloromethylphenylacetate used in Example 2.

Gaseous hydrogen chloride was bubbled through a solution of 3-isochromanone (2.0 g, 13.5 mmol) in methanol (30 ml) for 0.5 hour at room temperature and the reaction stirred for a further 2 hours. The methanol was removed under reduced pressure and the residue was dissolved in dichloromethane and dried. Removal of the solvent gave methyl 2-chloromethylphenylacetate (2.62 g, 98%) as an oil which was used without further purification; $^1$H NMR (270 MHz) δ: 3.70(3H,s), 3.81(2H,s), 4.68(2H,s), 7.22–7.40(4H,m) ppm.

EXAMPLE 5

This Example illustrates the preparation of methyl 2-(6-trifluoromethylpyrid-2-yloxymethyl)phenylacetate (Compound No.3 in Table 1) from 2-hydroxy-6-trifluoromethylpyridine and methyl 2-chloromethylphenylacetate in the presence of potassium carbonate.

A water wet paste of 2-hydroxy-6-trifluoromethylpyridine (16.7 g at 71.8% strength, 0.073 mol) and toluene (90 g) were charged to a 500 ml flask fitted with a still head and stirrer and heated to remove water by azeotropic distillation. Heating was continued until a head temperature of 110° C. was reached and approximately three quarters of the toluene had been removed. The remaining slurry was cooled to ambient temperature and DMF (40 g) and potassium carbonate (15.5 g) added. The reaction mixture was heated to 60–70° C. Methyl 2-chloromethylphenylacetate (17.4 g at 80.3% strength, 0.07 mol) dissolved in DMF (40 g) was added dropwise to the flask over 3 hours while the temperature was maintained at 70° C. The reaction mixture was then heated to 80° C. and held for 1 hour before being cooled to ambient temperature. Water (200 ml) was added and stirring continued for 15 minutes. Toluene (61 g) was added and the aqueous and toluene layers separated. The aqueous layer was extracted with toluene (61 g) twice more. The toluene layers were combined and washed with water (2×100 ml). Toluene was removed by vacuum distillation (40 mm Hg) to a maximum temperature of 60° C. The distillation was stopped before all of the toluene has been removed to leave approximately 40 g of the title product at 48.8% strength (86% yield).

EXAMPLE 6

This Example illustrates the preparation of methyl 2-(6-trifluoromethylpyrid-2-yloxymethyl)phenylacetate (Compound No.3 in Table 1) from the potassium salt of 2-hydroxy-6-trifluoromethylpyridine and methyl 2-chloromethylphenylacetate in the presence of water.

A water wet paste of 2-hydroxy-6-trifluoromethylpyridine (83 g at 60.25% strength, 0.0307 mol), potassium carbonate (6.0 g) and DMF (25 ml) were charged to a 250 ml flask fitted with a stirrer and heated to 70° C. Methyl 2-chloromethylphenylacetate (6.8 g at 85.0% strength, 0.0292 mol) dissolved in DMF (10 ml) was added dropwise in part over 50 minutes and the reaction mixture left to cool overnight. The reaction mixture was reheated to 70° C. and the remaining phenylacetate/DMF solution charged over 1¼ hours. The reaction mixture was then heated to 80° C. and stirred for 1 hour, before a sample being tested by gas chromatography for completion of reaction. The reaction mixture was cooled, water (50 ml) was added followed by toluene (33 ml) and stirring was continued for 15 minutes. The aqueous and toluene layers were then separated. The aqueous layer was extracted with toluene (2×33 ml). The extracts were combined with the toluene layer, washed with water (2×50 ml) and most of the toluene was removed by vacuum distillation to give 12.4 g the title product at 60.13% strength (yield 78.6%).

EXAMPLE 7

This Example further illustrates the preparation of methyl 2-(6-trifluoromethylpyrid-2-yloxymethyl)phenylacetate (Compound No. 3 in Table 1).

Toluene (130 kg) and 2-hydroxy-6-trifluoromethylpyridine, water-wet paste (17.3 kg at 100% strength) were charged to a 250 l reactor. The water was removed by azeotropic distillation. A total of 99.5 kg of distillate was removed. The slurry was cooled to 30° C. and DMF (58 kg) was added. The solution was transferred to a 750 l reactor followed by a line wash of DMF (10 kg). Potassium carbonate (22.5 kg) was charged to the reactor and the mixture heated to 60° C. Methyl 2-chloromethylphenylacetate (20.2 kg at 100% strength) was charged to a 250 l reactor with DMF (58 kg) and transferred into the reaction mixture over 4 hours at 60–70° C. The reaction mixture was heated to 80° C. and held for 2 hours then cooled to 30° C. Toluene (92 kg) and water (289 kg) were added to the reactor and the layers separated. The aqueous layer was extracted twice with toluene (2×92 kg) and the extracts combined. These extracts were washed with water (2×144 kg). Most of the toluene was removed by vacuum distillation to leave a toluene solution of the product (methyl 2-(6-trifluoromethylpyrid-2-yloxymethyl) phenylacetate) 61 kg at 51.7% strength 95.3% yield.

EXAMPLE 8

This Example further illustrates the preparation of methyl 2-(6-trifluoromethylpyrid-2-yloxymethyl)-phenylacetate (Compound No.3 in Table 1).

A water wet paste of 2-hydroxy-6-trifluoromethylpyridine (4.99 g at 60.2% strength, 0.018 mol) and toluene (22.5 g) were charged to a 250 ml round-bottomed flask and the water removed by azeotropic distillation to a still head temperature of 110° C. (19 g of toluene/water collected). The mixture was allowed to cool to room temperature and toluene (10 g) was added followed by potassium carbonate (3.91 g, 0.028 mol) and tetrabutylammonium iodide (0.33 g, 8.85. $10^{-4}$ mol). Further toluene (20 g) was added to obtain a mobile mixture and then methyl 2-chloromethylphenylacetate (4.02 g at 87.15% strength, 0.018 mol) in toluene (10 g) was added in a dropwise manner over 3.5 hours at 80° C. then held at this temperature for 1 hour. The solution was cooled to room temperature and water (25 ml) was added. Stirring was continued for 2 minutes and the water separated. The toluene was washed again with water (10 ml). Toluene and water were removed by azeotropic distillation (bath temperature 65° C.; still head temperature 47° C.; 85 mmHg) to give a solution of the title product in toluene: 18.99 g at 24.02% strength (yield 79.3% by GC).

EXAMPLE 9

This Example further illustrates the preparation of methyl 2-(6-trifluoromethylpyrid-2-yloxymethyl)-phenylacetate (Compound No.3 in Table 1).

A water wet paste of 2-hydroxy-6-trifluoromethylpyridine (4.17 g at 71.8% strength, 0.018 mol) and toluene (22.5 g) were charged to a 3-necked round-bottomed flask and distilled until all of the water and toluene were removed. Methyl 2-chloromethylphenylacetate (4.02 g at 87.15% strength, 0.0175 mol), potassium carbonate (3.87 g, 0.028 mol), butanone (25 g) and tetrabutylammonium iodide (0.33 g, 8.76. $10^{-4}$ mol) were added and left overnight at room temperature then heated at reflux for 6 hours. The butanone was removed by distillation and the remaining slurry partitioned between water (25 g) and toluene (22.5 g). The toluene layer was washed with water and then distilled under vacuum (65° C. bath temperature; 100 mmHg) to give a solution of the title product in toluene: 13.48 g at 36.14% strength (yield 85.7% by GC).

EXAMPLE 10

This Example further illustrates the preparation of methyl 2-(6-trifluoromethylpyrid-2-yloxymethyl)-phenylacetate (Compound No.3 in Table 1).

A water wet paste of 2-hydroxy-6-trifluoromethylpyridine (16.7 g at 71.8% strength, 0.073 mol) and toluene (90 g) were charged to a 500 ml round-bottomed flask and an azeotropic distillation carried out to a still head temperature of 100° C. (bath temperature 145° C.; weight of toluene/water collected, 84 g). The mixture was cooled to room temperature and DMF (40 g) and potassium carbonate (15.5 g, 0.112 mol) were added. The resulting suspension was heated with stirring to 70–75° C. and a solution of methyl 2-chloromethylphenylacetate (16.06 g at 87.15% strength, 0.07 mol) in DMF (40 g) was added over 3 hours. The reaction mixture was held at 80° C. for 1 hour before being cooled to room temperature and then distilled under vacuum to remove the DMF (85° C. bath temperature; 5 mmHg; 39.35 g DMF removed). Toluene (90 g) and water (100 g) were added and stirring continued for 2 minutes. The water was separated and the toluene extract washed with water (40 g). The organic extract was distilled (85° C.; 100 mmHg; 60 g of toluene/water collected) to give a solution of the title product in toluene: 62.02 g at 35.18% strength (yield 97.7% by GC).

CHEMICAL STRUCTURES

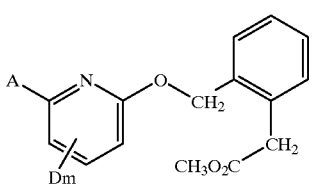
(I)

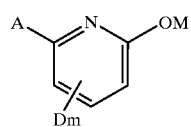
(II)

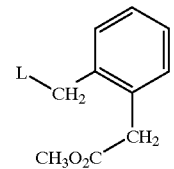
(III)

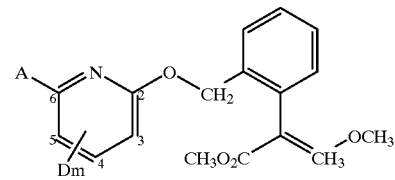
(IV)

We claim:

1. A process for the preparation of a compound of formula (I):

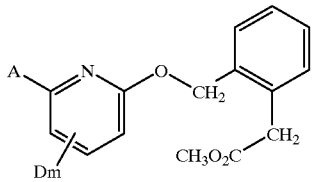
(I)

wherein A and D are independently selected from the group comprising halo, hydroxy, halo($C_{1-4}$)alkyl, $C_{1-4}$ alkoxy, thio ($C_{1-4}$)alkoxy, halo($C_{1-4}$) alkoxy, phenyl, phenoxy, nitro, amino, acylamino, cyano, carboxy, $C_{1-4}$ alkoxycarbonyl and $C_{1-4}$ alkylcarbonyloxy, or D is $C_{1-4}$ alkyl, and m is 0 or an integer of from 1 to 3, which comprises treating a compound of formula (II):

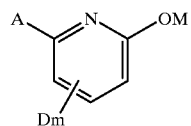
(II)

wherein A, D and m are as defined above and M is a metal atom, with a compound of formula (III):

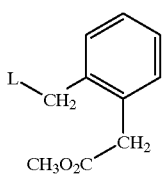
(III)

wherein L is a leaving group.

2. A process according to claim 1 wherein A and D are independently selected from the group comprising halo, halo($C_{1-4}$) alkyl and $C_{1-4}$ alkoxy, or D is $C_{1-4}$ alkyl, m is 0 or 1, and where m is 1, D is attached to the 4-position of the pyridine ring.

3. A process according to claim 1 wherein M is an alkali metal atom.

4. A process according to claim 1 wherein L is a halide, $CH_3SO_4$ or sulphonyloxy anion.

5. A process according to claim 1 wherein the compound of formula (II) is treated with the compound of formula (III) at a temperature of from 60 to 90° C.

6. A process according to claim 1 wherein the compound of formula (II) is treated with the compound of formula (III) in N,N-dimethylformamide.

7. A process according to claim 1 which comprises heating an appropriate 6-substituted 2-pyridine with potassium carbonate at an elevated temperature in a solvent, and treating the compound of formula (II) so formed wherein M is potassium with the compound of formula (III).

8. A compound of the formula (I) prepared by a process according to claim 1.

* * * * *